(12) United States Patent  (10) Patent No.: US 7,249,831 B2
Childers et al.  (45) Date of Patent: Jul. 31, 2007

(54) INK CONTAINER REFURBISHMENT SYSTEM

(75) Inventors: Winthrop D. Childers, San Diego, CA (US); Michael L. Bullock, San Diego, CA (US); Norman E. Pawlowski, Jr., Corvallis, OR (US); Jeffrey L. Thielman, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 10/426,332

(22) Filed: Apr. 30, 2003

(65) Prior Publication Data

US 2003/0206220 A1  Nov. 6, 2003

Related U.S. Application Data

(63) Continuation of application No. 09/951,114, filed on Sep. 13, 2001, now Pat. No. 7,008,050, and a continuation-in-part of application No. 08/869,023, filed on Jun. 4, 1997, now Pat. No. 6,017,118, which is a continuation-in-part of application No. 08/566,521, filed on Dec. 4, 1995, now abandoned, and a continuation-in-part of application No. 08/429,915, filed on Apr. 27, 1995, now Pat. No. 5,825,387, application No. 10/426,332, which is a continuation-in-part of application No. 08/984,219, filed on Dec. 3, 1997, now Pat. No. 6,074,050, application No. 10/426,332, and a continuation-in-part of application No. 09/034,719, filed on Mar. 4, 1998, now Pat. No. 6,170,937, which is a continuation-in-part of application No. 08/785,580, filed on Jan. 21, 1997, now Pat. No. 5,812,156, application No. 10/426,332, which is a continuation-in-part of application No. 09/053,556, filed on Apr. 1, 1998, now Pat. No. 6,015,209, which is a continuation-in-part of application No. 08/566,821, filed on Dec. 4, 1995, now Pat. No. 5,777,646.

(51) Int. Cl.
    *B41J 2/175* (2006.01)
(52) U.S. Cl. ....................................................... 347/85
(58) Field of Classification Search .................. 347/7, 347/19, 86, 87, 85; 141/2, 18
    See application file for complete search history.

(56) References Cited

U.S. PATENT DOCUMENTS

| 4,558,326 | A | * | 12/1985 | Kimura et al. ............... 347/30 |
| 4,568,954 | A | | 2/1986 | Rosback |
| 4,677,448 | A | | 6/1987 | Mizusawa et al. |
| 4,967,207 | A | | 10/1990 | Ruder |
| 5,068,806 | A | | 11/1991 | Gatten |
| 5,414,452 | A | | 5/1995 | Accatino et al. |
| 5,506,611 | A | | 4/1996 | Ujita et al. |
| 5,610,635 | A | * | 3/1997 | Murray et al. ............... 347/7 |
| 5,663,754 | A | | 9/1997 | Lorenze, Jr. et al. |
| 5,699,091 | A | | 12/1997 | Bullock et al. |
| 5,721,576 | A | | 2/1998 | Barinaga |
| 5,732,751 | A | | 3/1998 | Schmidt et al. |
| 5,784,087 | A | | 7/1998 | Wallace |

(Continued)

FOREIGN PATENT DOCUMENTS

DE  29502908.O  3/1995

(Continued)

*Primary Examiner*—Anh T. N. Vo

(57) ABSTRACT

Alternative methods for refurbishing a single-use ink delivery container for a printing system are described. The refurbishing methods include electrical and mechanical reconfiguration or replacement of original elements on the ink delivery container. Each method utilizes an existing ink fluid outlet, electrical connector and an information storage device on the ink delivery container.

17 Claims, 13 Drawing Sheets

U.S. PATENT DOCUMENTS

| | | |
|---|---|---|
| 5,852,459 A | 12/1998 | Pawlowski |
| 5,950,403 A | 9/1999 | Yamaguchi et al. |
| 6,017,118 A | 1/2000 | Gasvoda et al. |
| 6,074,050 A | 6/2000 | Perez et al. |
| 6,318,850 B1 * | 11/2001 | Childers et al. ............... 347/85 |
| 7,008,050 B2 * | 3/2006 | Childers et al. ............... 347/85 |

FOREIGN PATENT DOCUMENTS

| | | | |
|---|---|---|---|
| EP | 0498117 | A2 | 8/1992 |
| EP | 0720916 | A2 | 7/1996 |
| EP | 0778144 | A1 | 6/1997 |
| EP | 0789322 | A2 | 8/1997 |
| EP | 0803364 | A2 | 10/1997 |
| JP | 03016737 | | 1/1991 |
| JP | 5-318760 | | 12/1993 |
| JP | 60154074 | | 1/1994 |
| JP | 06064182 | | 3/1994 |
| JP | 06106729 | | 4/1994 |
| JP | 09039262 | | 2/1997 |
| JP | 09039262 | A | 2/1997 |
| JP | 11291517 | A | 10/1999 |
| WO | WO 85/00454 | | 1/1985 |
| WO | WO 97/45269 | | 4/1997 |
| WO | WO 98/22290 | | 5/1998 |

* cited by examiner

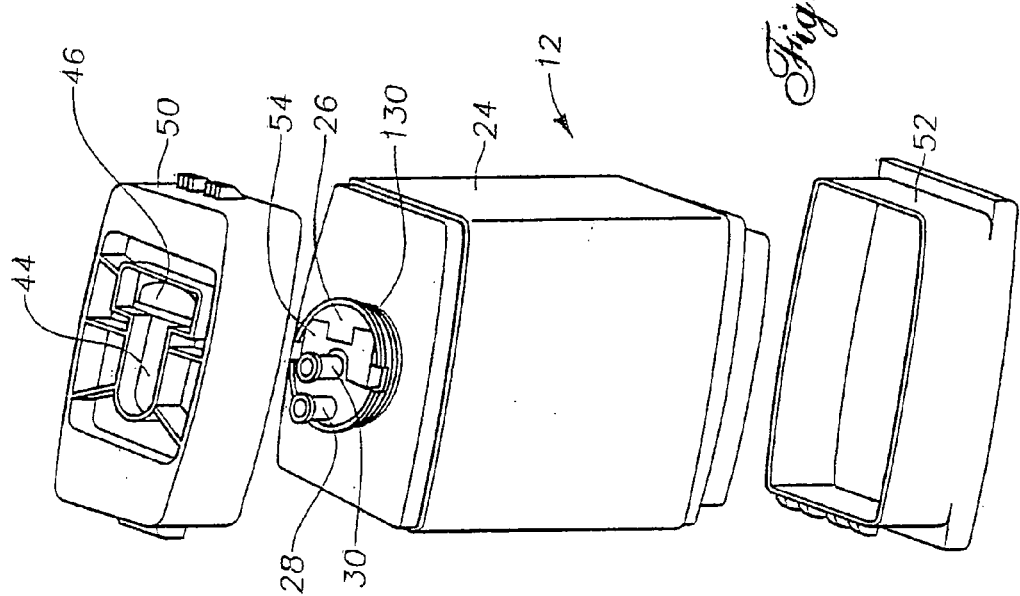
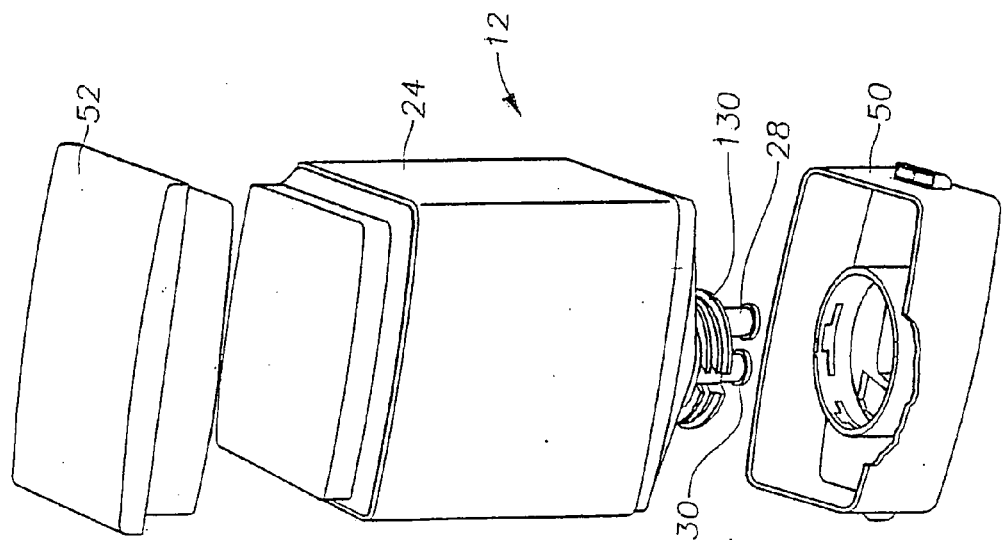

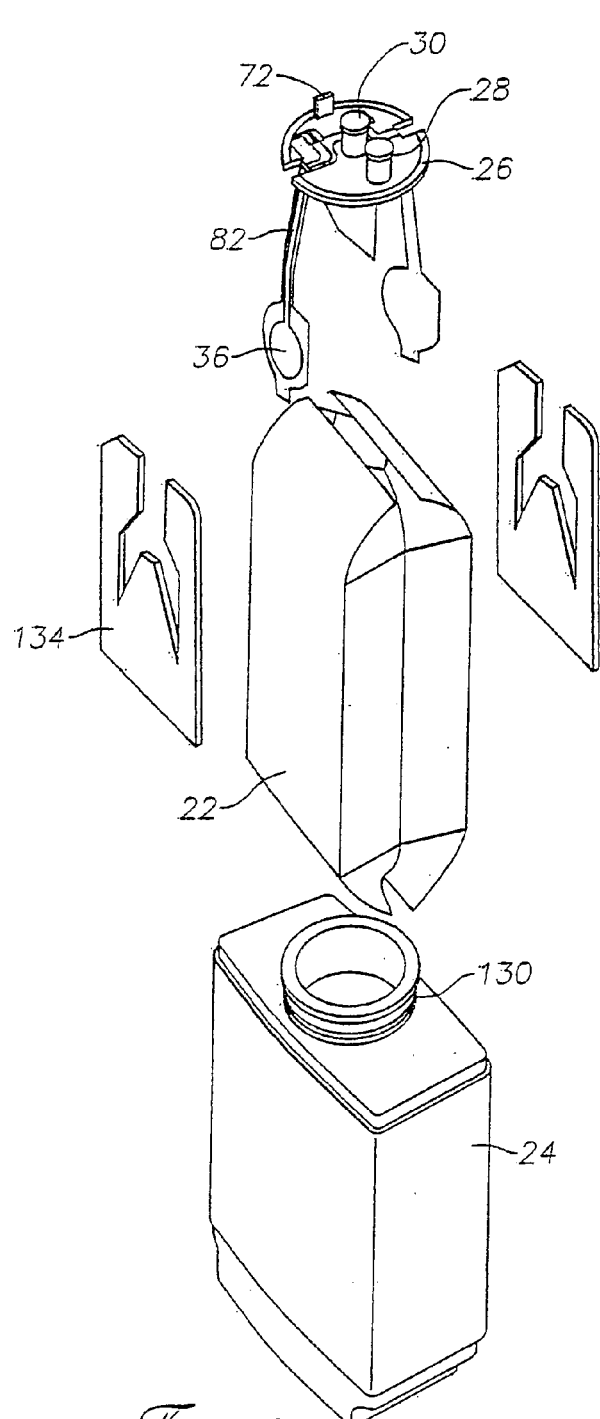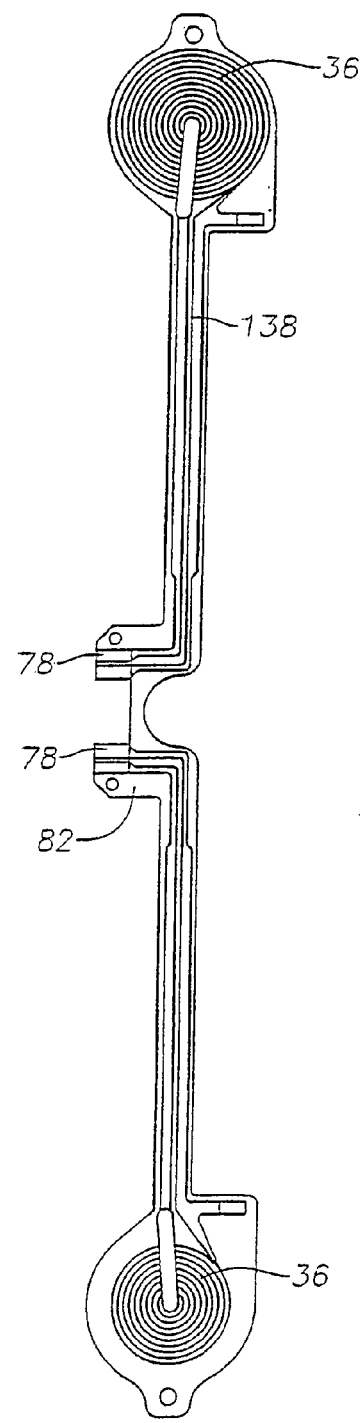
Fig. 12
Fig. 13

INK CONTAINER REFURBISHMENT SYSTEM

This application is a continuation-in-part of Ser. No. 08/869,023, filed Jun. 04, 1997, now U.S. Pat. No. 6,017,118 entitled "High Performance Ink Container With Efficient Construction" issued Jan. 25, 2000 which is a continuation-in-part of U.S. patent application Ser. No. 08/566,521 filed Dec. 4, 1995, entitled "Keying System For Ink Supply Containers", abandoned, and Ser. No. 08/429,915, filed Apr. 27, 1995, now U.S. Pat. No. 5,825,387 entitled "Ink Supply For An Inkjet Printer" issued Oct. 20, 1998. This application is also a continuation-in-part of Ser. No. 08/984,219 filed Dec. 03, 1997, now U.S. Pat. No. 6,074,050 entitled "Method And Apparatus For Venting An Ink Container" issued Jun. 13, 2000. This application is also a continuation-in-part of Ser. No. 09/034,719 filed Mar. 04, 1998, now U.S. Pat. No. 6,170,937 entitled, "Ink Container Refurbishment Method" issued Jan. 9, 2001 which is a continuation-in-part of Ser. No. 08/785,580 filed Jan. 21, 1997, now U.S. Pat. No. 5,812,156, entitled "Apparatus Controlled by Data From Consumable Parts With Incorporated Memory Devices" issued Sep. 22, 1998. This application is also a continuation-in-part of Ser. No. 09/053,556 filed Apr. 01, 1998, now U.S. Pat. No. 6,015,209, entitled "Replaceable Ink Container with Fluid Interconnect for Coupling to an Ink-jet Printer" issued Jan. 18, 2000 which is a continuation-in-part of Ser. No. 08/566,821 filed Dec. 04, 1995, now U.S. Pat. No. 5,777,646, entitled "Self-Sealing Fluid Interconnect with Double Sealing Septum", issued Jul. 7, 1998. In addition, this application is related to commonly assigned U.S. patent application Ser. No. 09/034,874 filed Mar. 4, 1998, entitled "Ink Delivery System Adapter", U.S. patent application Ser. No. 09/034,875 filed Mar. 4, 1998, entitled "Electrical Refurbishment for Ink Delivery System", and to U.S. patent application Ser. No. 09/125,086, entitled "Large Capacity Ink Delivery System Adapter" filed herewith.

TECHNICAL FIELD

This invention relates in general to ink-jet printing systems, and in particular to refurbishing ink containers for ink-jet printing systems.

BACKGROUND ART

One type of prior art ink-jet printer has a printhead mounted to a carriage which is moved back and forth over print media, such as paper. As the printhead passes over appropriate locations on the print media, a control system activates the printhead to eject ink drops onto the print media and form desired images and characters. To work properly, such printers should have a reliable supply of ink for the printhead.

One category of ink-jet printer uses an ink supply that is mounted to and moves with the carriage. In some types, the ink supply is replaceable separately from the printhead. In others, the printhead and ink supply together form an integral unit that is replaced as a unit once the ink in the ink supply is depleted.

Another category of printer, referred to as an "off-axis" printing system, uses ink supplies which are not located on the carriage. One type replenishes the printhead intermittently. The printhead will travel to a stationary reservoir periodically for replenishment. U.S. patent application Ser. No. 09/034,719 describes another printing system wherein the printhead is fluidically coupled to a replaceable ink supply or container via a conduit such as a flexible tube. This allows the printhead to be continuously replenished during a printing operation.

In the parent application to this application, a replaceable off-axis ink container is described which has a memory device mounted to the housing. When inserted into the printer station, an electrical connection between the printer and the memory device is established. This electrical connection allows for the exchange of information between the printer and the memory. The memory device stores information which is utilized by the printer to ensure high print quality. This information is provided to the printer automatically when the cartridge is mounted to the printer. The exchange of information assures compatibility of the cartridge with the printer.

The stored information further prevents the use of the container after it is depleted of ink. Operating a printer when the reservoir has been depleted of ink may damage or destroy the printhead. The memory devices concerned with this application are updated with data from the printhead concerning the amount of ink left in the reservoir as it is being used. When a new cartridge is installed, the printer will read information from the memory device that is indicative of the reservoir volume. During usage, the printing system estimates ink usage and updates the memory device to indicate remaining ink in the cartridge. Once the ink in the ink container is substantially depleted, the memory device is updated to reflect an out-of-ink condition. The depleted of ink cartridges and memory devices are then discarded.

DISCLOSURE OF THE INVENTION

The present invention comprises alternative methods for refurbishing a single-use ink delivery container for a printing system. The refurbishing methods include electrical and mechanical reconfiguration or replacement of original elements on the ink delivery container. Each method utilizes an existing ink fluid outlet, electrical connector and an information storage device on the ink delivery container.

BRIEF DESCRIPTION OF THE DRAWINGS

FIG. 11A is a partially exploded isometric view of the ink container of FIGS. 10A, 10B, as shown from the distal end.

FIG. 11B is a partially exploded isometric view of the ink container of FIGS. 10A, 10B, as shown from the proximal end.

FIG. 12 is a further exploded isometric view of the ink container of FIGS. 10A, 10B.

FIG. 13 is an enlarged side view showing the inductive fluid level sensors for the ink container of FIGS. 10A, 10B, shown detached from the ink container.

BEST MODE FOR CARRYING OUT THE INVENTION

Although the present invention comprises methods for refurbishing ink containers, the invention may be more clearly understood with a thorough discussion of the printer and original equipment ink container.

Figure 1:
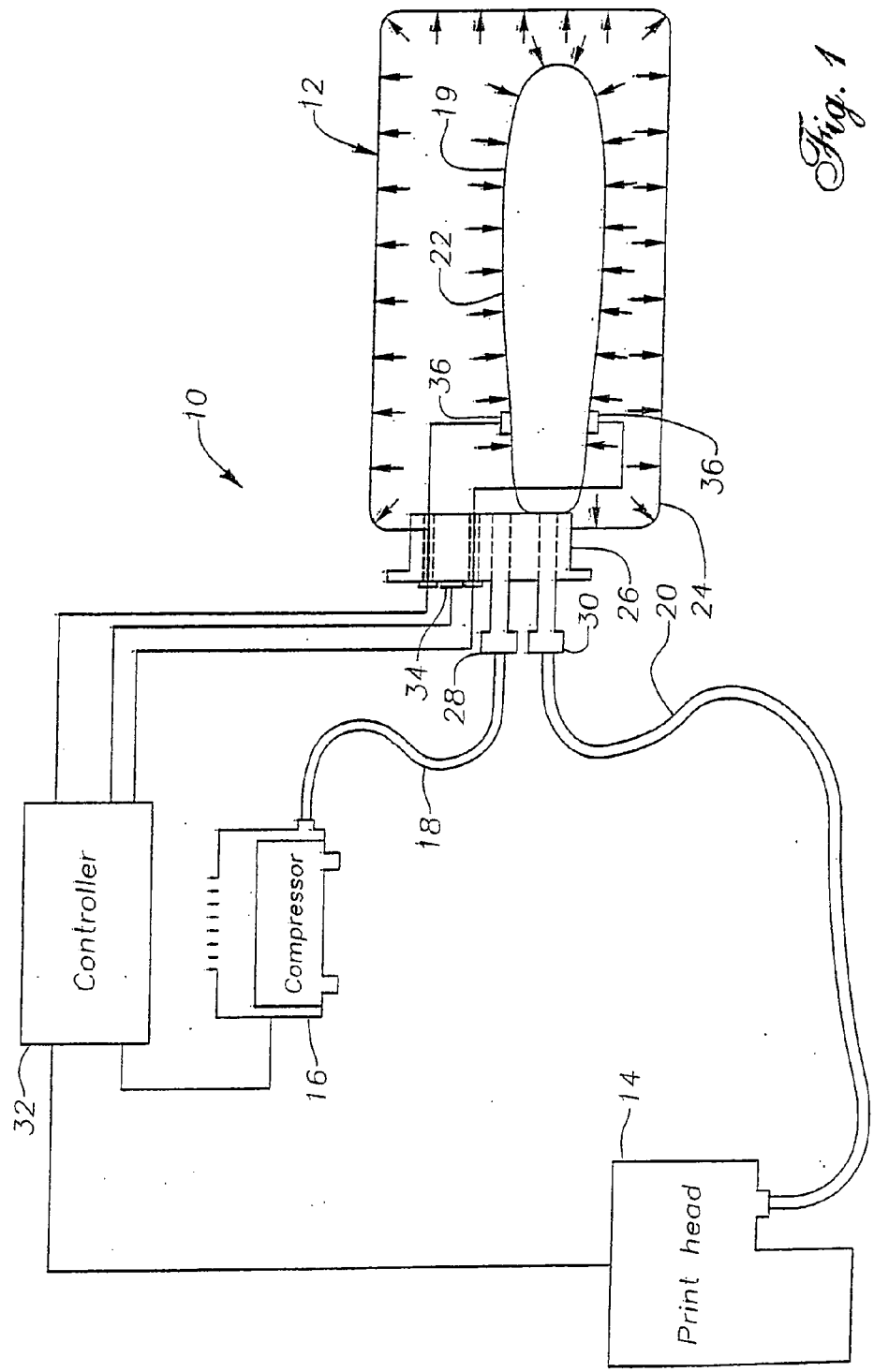
FIG. 1 is a schematic drawing of a printing system having an original equipment ink delivery system.

Referring to FIG. 1, a printing system 10 having an ink container 12, a printhead 14 and a source of pressurized gas, such as a compressor 16, is shown. Compressor 16 is connected to ink container 12 with a conduit 18. A marking fluid 19 such as ink is provided by ink container 12 to printhead 14 by a conduit 20. Ink container 12 includes a fluid reservoir 22 for containing ink 19, an outer shell 24, and a chassis 26. In the preferred embodiment, chassis 26 includes air inlet 28 configured for connection to conduit 18 for pressurizing the outer shell 24 with air. A fluid outlet 30 is also included in the chassis 26. The fluid outlet 30 is configured for connection to the conduit 20 for providing a connection between the fluid reservoir 22 and fluid conduit 20.

In the preferred embodiment, the fluid reservoir 22 is formed from a flexible material such that pressurization of outer shell 24 produces a pressurized flow of ink from the fluid reservoir 22 through the conduit 20 to the printhead 14. The use of a pressurized source of ink in the fluid reservoir 22 allows for a relatively high fluid flow rate from the fluid reservoir 22 to the printhead 14. The use of high flow rates or high rates of ink delivery to the printhead make it possible for high throughput printing by the printing system 10.

The ink container 12 also includes a plurality of electrical contacts, as will be discussed in more detail subsequently. The electrical contacts provide electrical connection between circuitry on ink container 12 and printer control electronics 32. The printhead control electronics 32 control various printing system 10 functions such as, but not limited to, printhead 14 activation to dispense ink and activate pump 16 to pressurize the ink container 12. Ink container 12 includes an information storage device 34 and ink volume sensing circuitry 36. The information storage device 34 provides information to the printer control electronics 32 such as ink container 12 volume as well as ink characteristics. The ink volume sensing circuitry 36 provides signals relating to current ink volume in ink container 12 to the printer control electronics 32.

Figure 2:
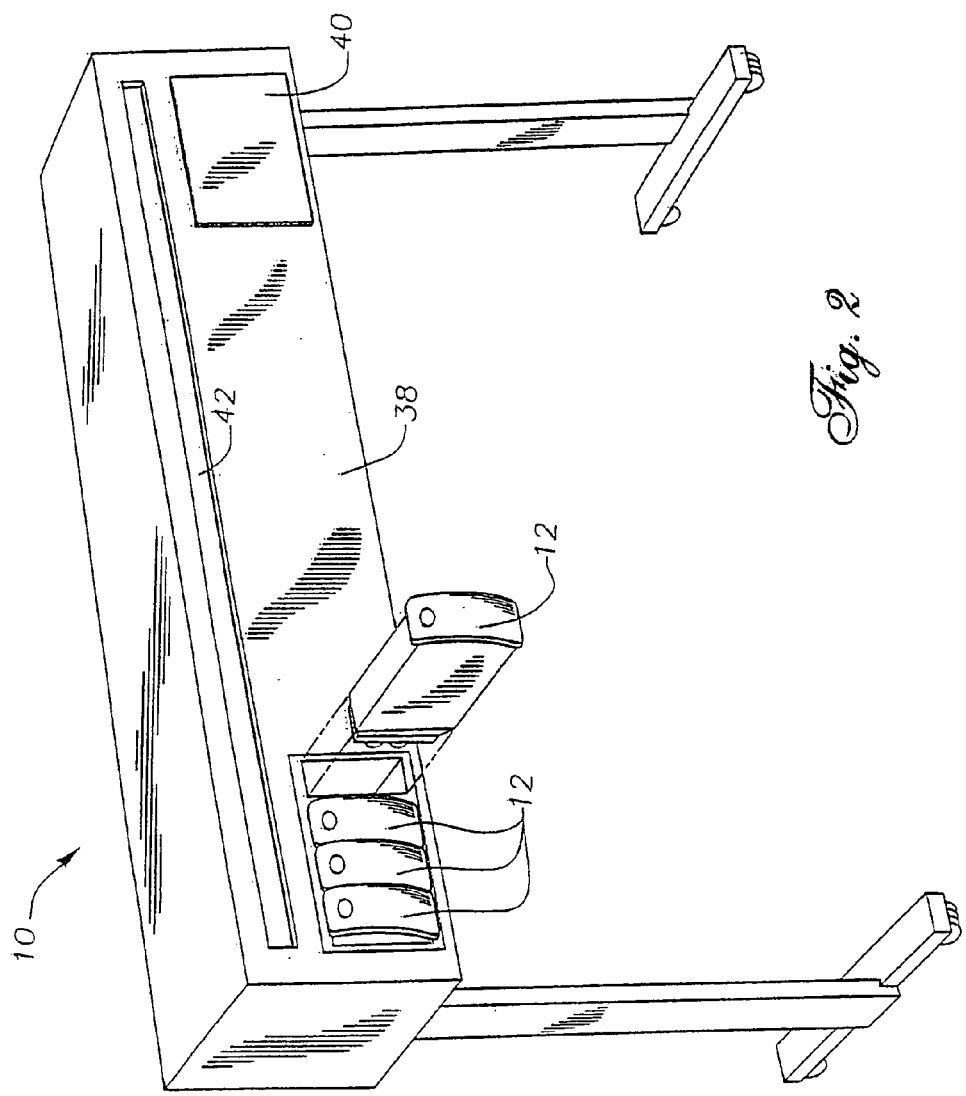
FIG. 2 is an isometric view of a printer incorporating the printing system as described with respect to FIG. 1.

FIG. 2 depicts one embodiment of printing system 10 shown in perspective. Printing system 10 includes a printing frame 38 constructed for containing several ink containers 12 simultaneously. The embodiment shown in FIG. 2 has four similar ink containers 12. In this embodiment, each ink container contains a different ink color so that four color printing can be accomplished using cyan, yellow, magenta and black inks. Printer frame 38 has a control panel 40 for controlling operation of printer 10 and a media slot 42 from which paper is ejected.

Referring also, to FIG. 1, as ink 19 in each ink container 12 is exhausted, container 12 is replaced with a new ink container 12 containing a new supply of ink. In addition, ink containers 12 may be removed from the printer frame 38 for reasons other than an out of ink condition such as changing inks for an application requiring different ink properties or for use on different media. It is important that the replacement ink container 12 form reliable electrical connection with corresponding electrical contacts associated with the printer frame 38 as well as properly form necessary interconnects so that printing system 10 performs reliably.

Figure 3:
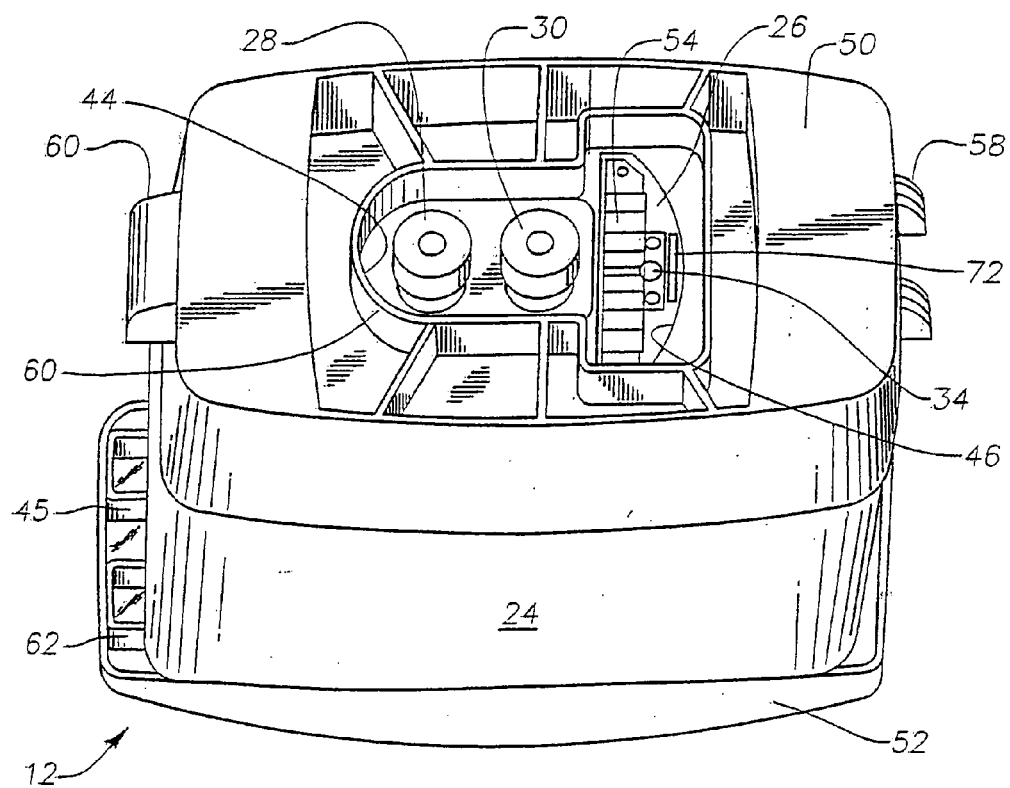
FIG. 3 is an end isometric view of an ink container of the printing system of FIG. 1.
Figure 4:
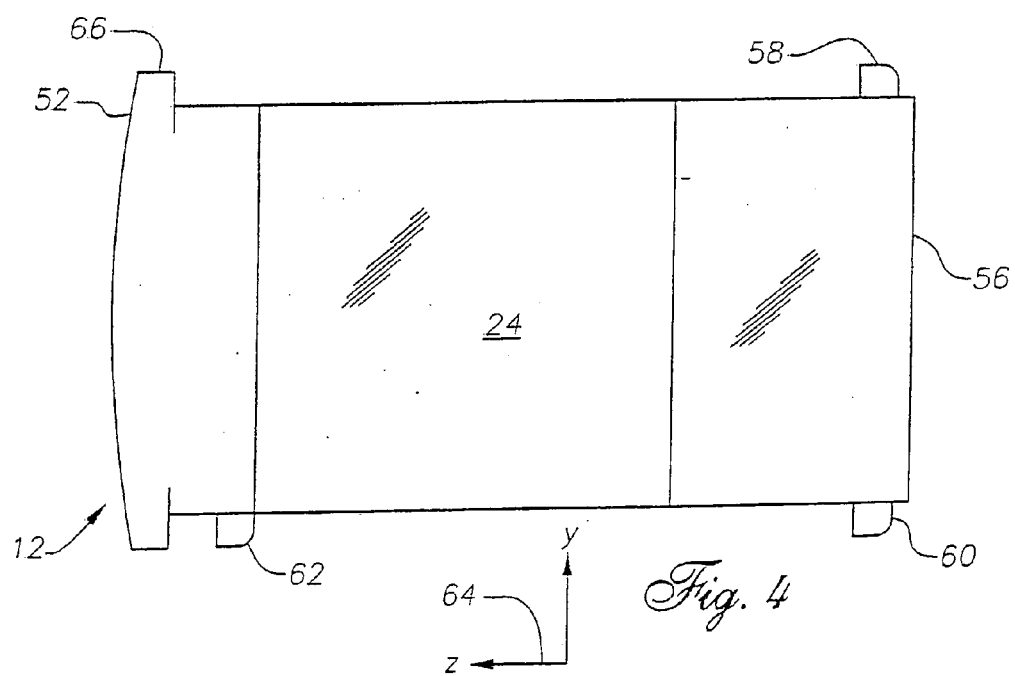
FIG. 4 is a side view of the ink container of FIG. 3.

FIGS. 3 and 4 depict an original equipment ink container 12 having an outer shell 24 which contains the fluid reservoir 22 (FIG. 1) for containing ink 19. Outer shell 24 has a leading cap 50 secured on a leading end and a trailing cap 52 secured on a trailing end, relative to a direction of insertion for the ink container 12 into the printer frame 38. Leading cap 50 has an aperture 44 on its leading end through which air inlet 28 and fluid outlet 30 from reservoir 22 (FIG. 1) protrudes. Reservoir chassis 26 has an end or base which abuts leading cap 50 so that air inlet 28 and ink outlet 30 protrude through aperture 44. Aperture 44 is surrounded by a wall 45, placing aperture 44 within a recess. Air inlet 28 and fluid outlet 30 are configured for connection to compressor 16 and printhead 14, respectively, (FIG. 1) once ink container 12 is properly inserted into the printer frame 38. Air inlet 28 and fluid outlet 30 will be discussed in more detail subsequently.

Leading cap 50 also has another aperture 46 which is located within the recess surrounded by wall 45. The base or end of chassis 26 is also exposed to aperture 46. A plurality of flat electrical contact pads 54 are disposed on reservoir chassis 26 and positioned within aperture 46 for providing electrical connection between circuitry associated with the ink container 12 and printer control electronics 32. Contact pads 54 are rectangular and arranged in a straight row. Four of the contact pads 54 are electrically connected to information storage device 34 and four are electrically interconnected to ink volume sensing circuitry 36 described with respect to FIG. 1. In a preferred embodiment, information storage device 34 is a semiconductor memory and the ink volume sensing circuitry 36 comprises an inductive sensing device. Wall 45 helps protect information storage device 34 and contact pads 54 from mechanical damage. In addition, wall 45 helps minimize inadvertent finger contact with contact pads 54. Contact pads 54 will be discussed in more detail with respect to FIG. 5.

In a preferred embodiment, ink container 12 includes one or more keying and guiding features 58 and 60 disposed on opposite sides of leading cap 50 of container 12. Keying and guiding features 58 and 60 protrude outward from sides of container 12 to work in conjunction with corresponding keying and guiding features or slots on the printer frame 38 (FIG. 2) to assist in aligning and guiding the ink container 12 during insertion of the ink container 12 into the printer frame 38. Keying and guiding features 58 and 60 also provide a keying function to insure that ink containers 12 having proper ink parameters, such as proper color and ink type, when inserted into a given slot in printer frame 38.

A latch shoulder 62 is provided on one side of trailing cap 52. Latch shoulder 62 works in conjunction with corresponding latching features on the printer portion to secure the ink container 12 within the printer frame 38 so that interconnects such as pressurized air, fluidic and electrical are accomplished in a reliable manner. Latch shoulder 62 is a molded tang which extends downwardly relative to a gravitational frame of reference. Ink container 12 as shown in FIG. 4 is positioned for insertion into a printer frame 38 (FIG. 2) along the Z-axis of coordinate system 64. In this orientation gravitational forces on the ink container 12 are along the Y-axis.

Figure 5:
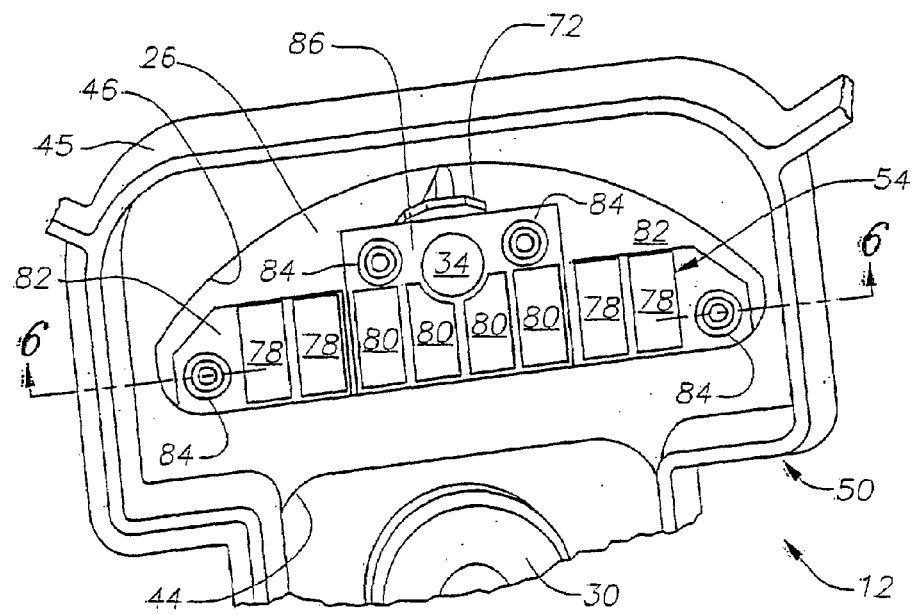
FIG. 5 is a partial enlarged proximal end view of the ink container of FIG. 3.

FIG. 5 depicts an enlarged view of electrical contact pads 54. An upstanding guide member 72 is mounted to chassis 26 adjacent contact pads 54. Electrical contact pads 54 include two pairs of contact pads 78, each pair being electrically connected to one of the volume sensing circuits 36, shown in FIG. 1. The four contact pads 80 spaced between each pair of pads 78 and contact pads 80 are electrically connected to the information storage device 34. Each pair of volume sensing contact pads 78 is located on an outer side of the row of contact pads 54. Contact pads 78 are part of a flexible circuit 82 (FIG. 13) which is mounted to the chassis 26 by fasteners 84. The four intermediate contacts 80 located between the pairs of volume sensing contacts 78 are metal conductive layers disposed on a nonconductive substrate 86 such as epoxy and fiberglass. Memory device 34 is also mounted on substrate 86 and is connected by conductive traces (not shown) formed in substrate 86. Memory device 34 is shown encapsulated by a protective coating such as epoxy. A backside of substrate 86, opposite contacts 80, is bonded by adhesive or attached to the chassis 26 by fasteners 84.

Figure 6:
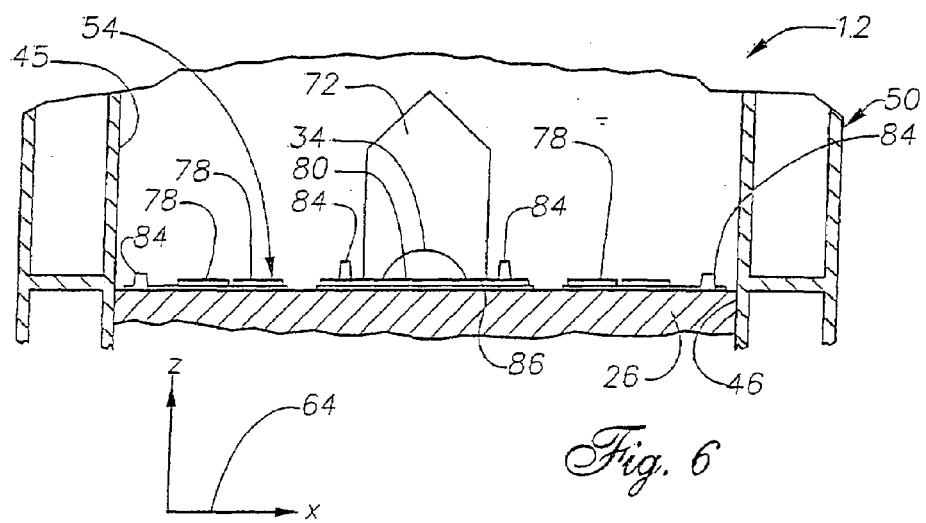
FIG. 6 is a sectional side view of the ink container of FIG. 3 taken along the line 6-6 of FIG. 5.
Figure 7:
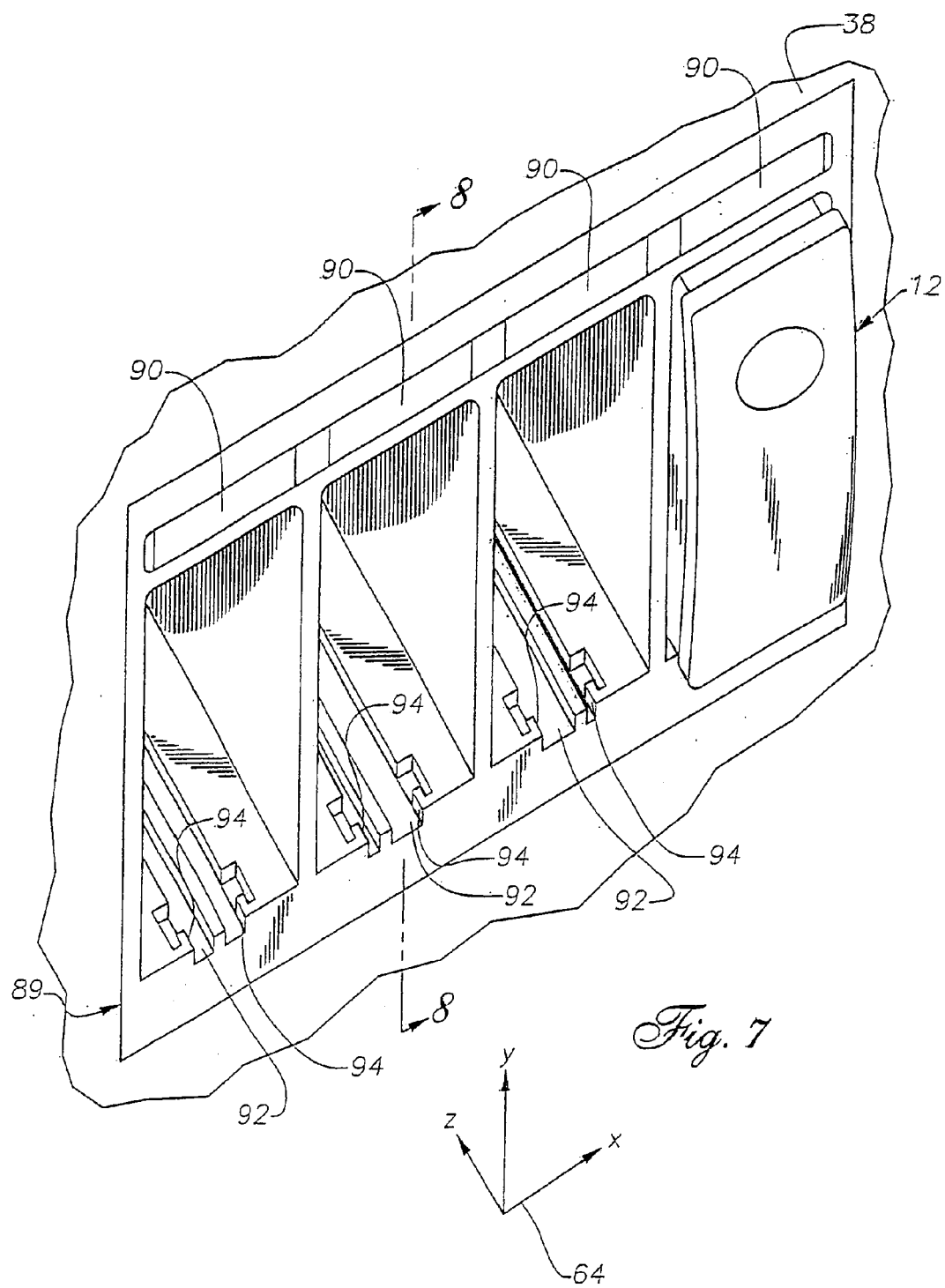
FIG. 7 is a partial enlarged isometric view of a portion of the printer of FIG. 2, showing the ink container receptacles.

It can be seen from FIG. 6 that the guide member 72 extends along a Z-axis in coordinate system 64. Guide member 72 has a pointed, tapered distal end. Guide member 72 provides an important guiding function to insure proper electrical connection is accomplished during the insertion of ink container 12 into the printer frame 38. FIG. 7 depicts one ink container 12 shown secured within an ink container receptacle or receiving slot 88 of receiving station 89 within the printer frame 38. Ink container indicia 90 may be positioned proximate each ink container receptacle 88. The ink container indicia 90 may be a color swatch or text indicating ink color to assist the user in color matching for inserting the ink container 12 in the proper slot 88 within the ink container receiving station 89. As discussed previously, the keying and guiding features 58 and 60 shown in FIGS. 3 and 4 prevent ink containers 12 from being installed in the wrong slot 88. Installation of an ink container 12 in the wrong receptacle 88 can result in improper color mixing or the mixing of inks of different ink types each of which can result in poor print quality.

Each receiving slot 88 within the ink container receiving station 89 includes keying and guiding features or slots 92 and a latching portion 94. Keying and guiding slots 92 cooperate with the keying and guiding feature 60 (FIG. 3) to guide ink container 12 into the ink container receiving station 89. The keying and guiding slot 92 corresponding to the keying and guiding feature 58 (FIG. 3) on ink container 12 is not shown. Latch portion 94 is configured for engaging the corresponding latch feature 62 on the ink container 12. The geometries of keying and guiding slots 92 vary from one receptacle 88 to the other to assure compatibility between ink containers and receptacles.

Figure 8:
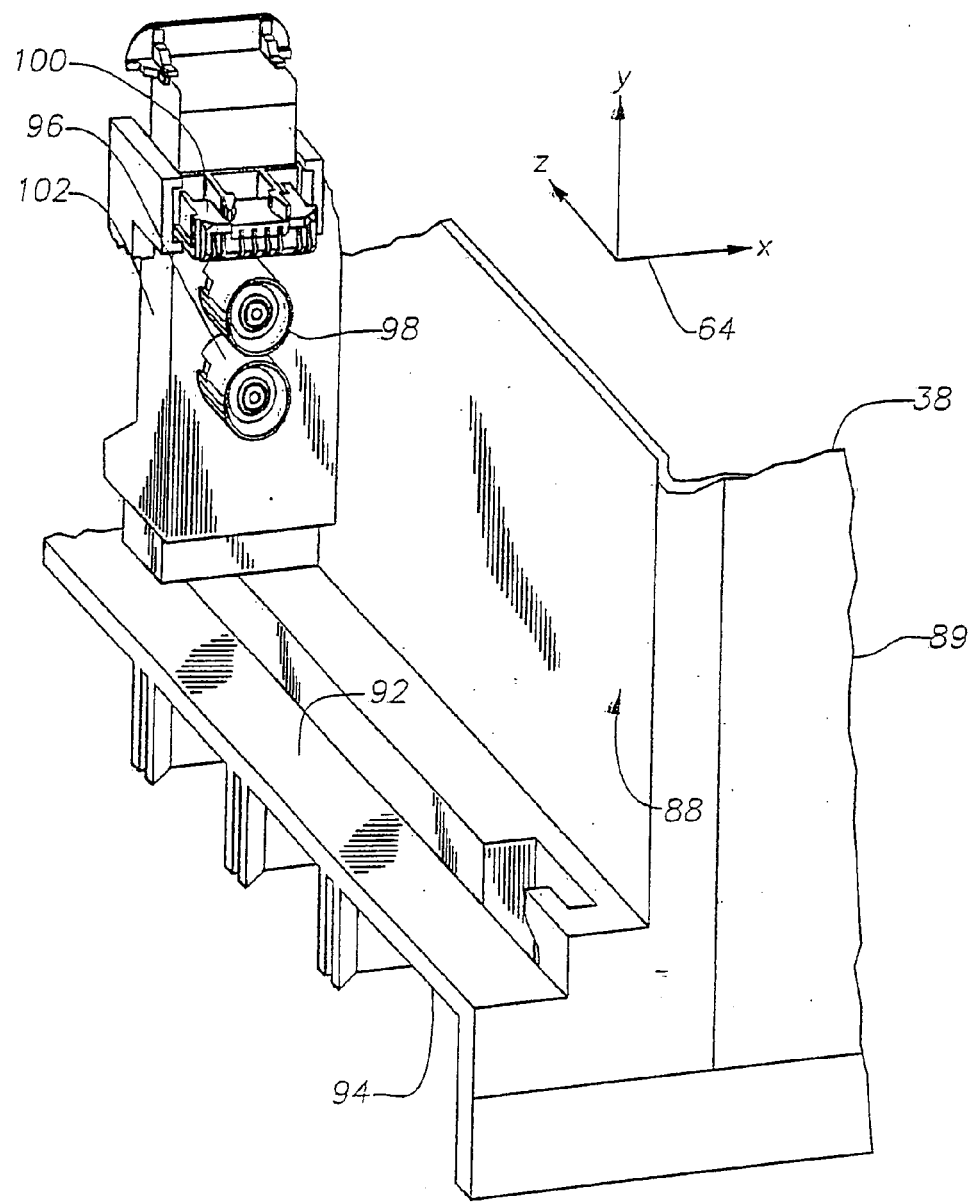
FIG. 8 is an enlarged partial isometric and sectional view of the printer of FIG. 2 taken along the line 8-8 of FIG. 7.

FIG. 8 shows a single ink container receiving slot 88 within the ink container receiving station 89. Slot 88 includes interconnect portions for interconnecting with the ink container 12. In the preferred embodiment these interconnect portions include a fluid inlet 98, and air outlet 96 and an electrical interconnect portion 100. Each of the interconnects 96, 98, and 100 are positioned on a floating platform 102 which is biased by coil springs 101 (FIG. 10A) along the Z-axis toward the installed ink container 12. Fluid inlet 98 and air outlet 96 are configured for connection with the corresponding fluid outlet 30 and air inlet 28 (FIG. 3), respectively on the ink container 12. The electrical interconnect 100 is configured for engaging electrical contacts 54 on the ink container 12.

It is the interaction between the keying and guiding features 58 and 60 associated with the ink container 12 and the corresponding keying and guiding feature 92 associated with the ink container receiving station 89 which guide the ink container 12 during the insertion such that proper interconnection is accomplished between the ink container 12 and the printer frame 38. In addition, sidewalls associated with each slot 88 in the ink container receiving station 89 engage corresponding sidewalls of the ink container 12 to assist in guiding and aligning ink container 12 during insertion into slot 88.

Figure 9:
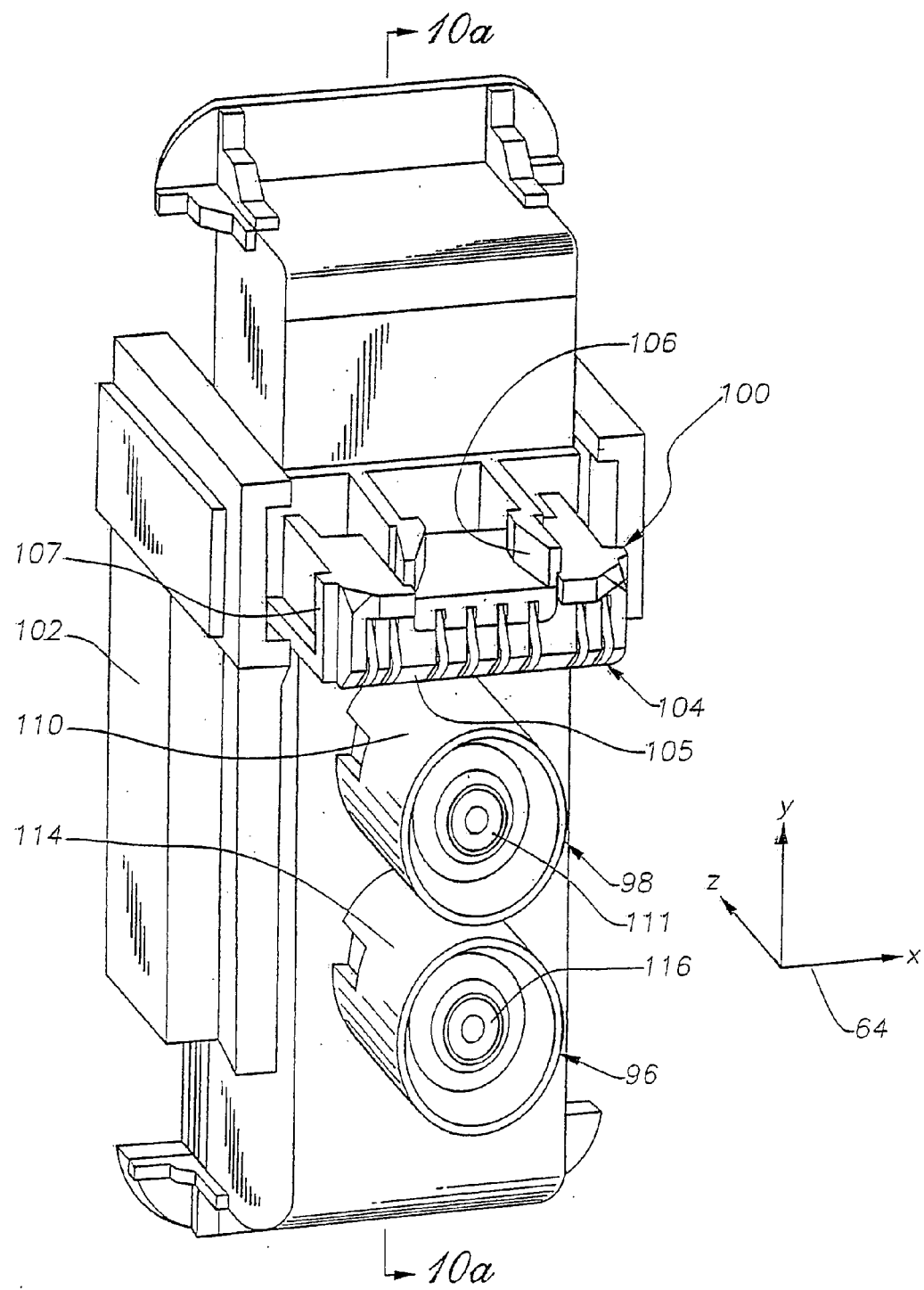
FIG. 9 is an enlarged isometric view of an interface portion of the printer of FIG. 2.
Figure 10A:
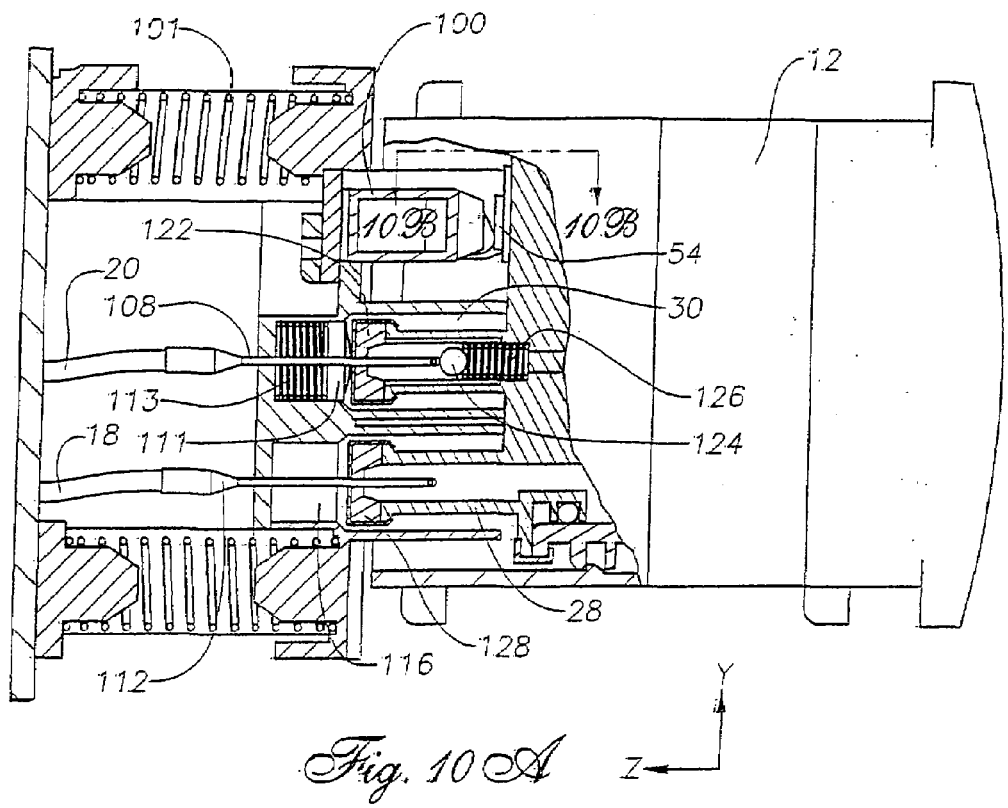
FIG. 10A is a partial sectional view of the interface portion of the printer which is shown in FIG. 9 taken along the line 10A-10A of FIG. 9 and showing also a partial sectional view of the ink container installed.

FIGS. 9 and 10A illustrate further details of the floating platform 102. Platform 102 is spring biased by coil springs 101 in a direction opposite the direction of insertion of the ink container 12 into the ink container receiving slot 88 (FIG. 10A). Platform 102 is biased towards mechanical restraints (not shown) which limit the motion of platform 102 in each of the X, Y, and Z axes. Therefore, platform 102 has a limited degree of motion in each of the X, Y, and Z axes of coordinate system 64.

Figure 10B:
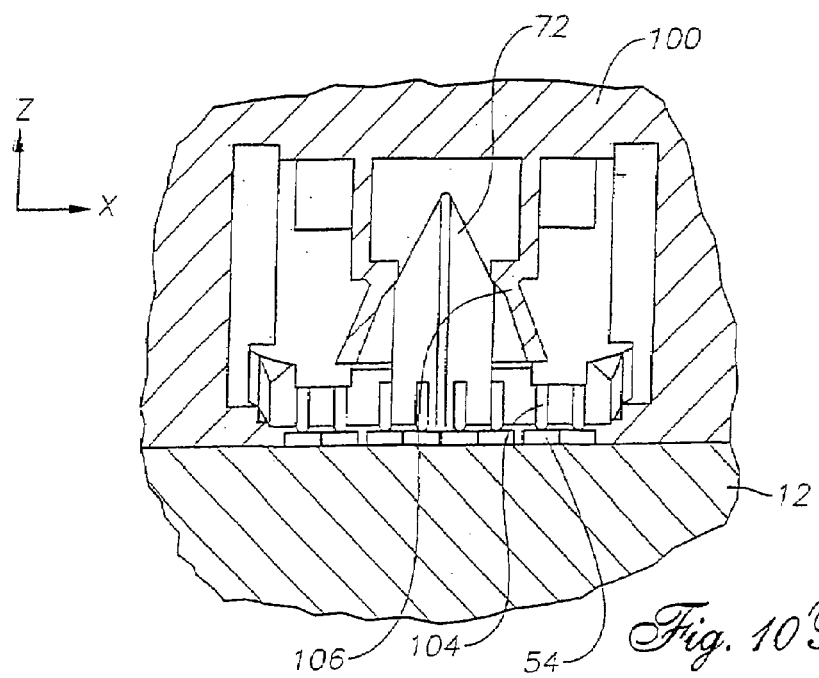
FIG. 10B is an enlarged view of the printer of FIG. 10A, taken along the line 10B-10B of FIG. 10A.

Electrical connector 100 is supported by and protrudes from platform 102. Electrical connector 100 is generally rectangular, having two lateral sides 107, upper and lower sides, and a distal end 105. A plurality of resilient, spring-biased electrical contacts 104 protrude from end 105. Electrical contacts 104 are thin wire-like members which engage corresponding electrical contacts 54 (FIG. 3) associated with ink container 12 to electrically connect ink container 12 with the printer controller 32 (FIG. 1). Electrical connector 100 has a guide slot 106 on its upper side. Guide slot 106 has opposed converging walls which cooperate to engage guide member 72 (FIGS. 5 and 10B). Guide member 72 engages guide slot 106 to properly align contacts 104 with contact pads 54. FIG. 10B shows contact pads 54 properly aligned with electrical contacts 104.

Referring to FIGS. 9 and 10A, fluid inlet 98 and air outlet 96 protrude from floating platform 102. Fluid inlet 98 includes an ink supply sleeve 110 surrounding a conduit 108. Needle 108 has a port near its distal end. A collar 111 sealingly and slidingly engages needle 108. A spring 113 urges collar 111 toward the distal end, blocking the port.

Figure 14:
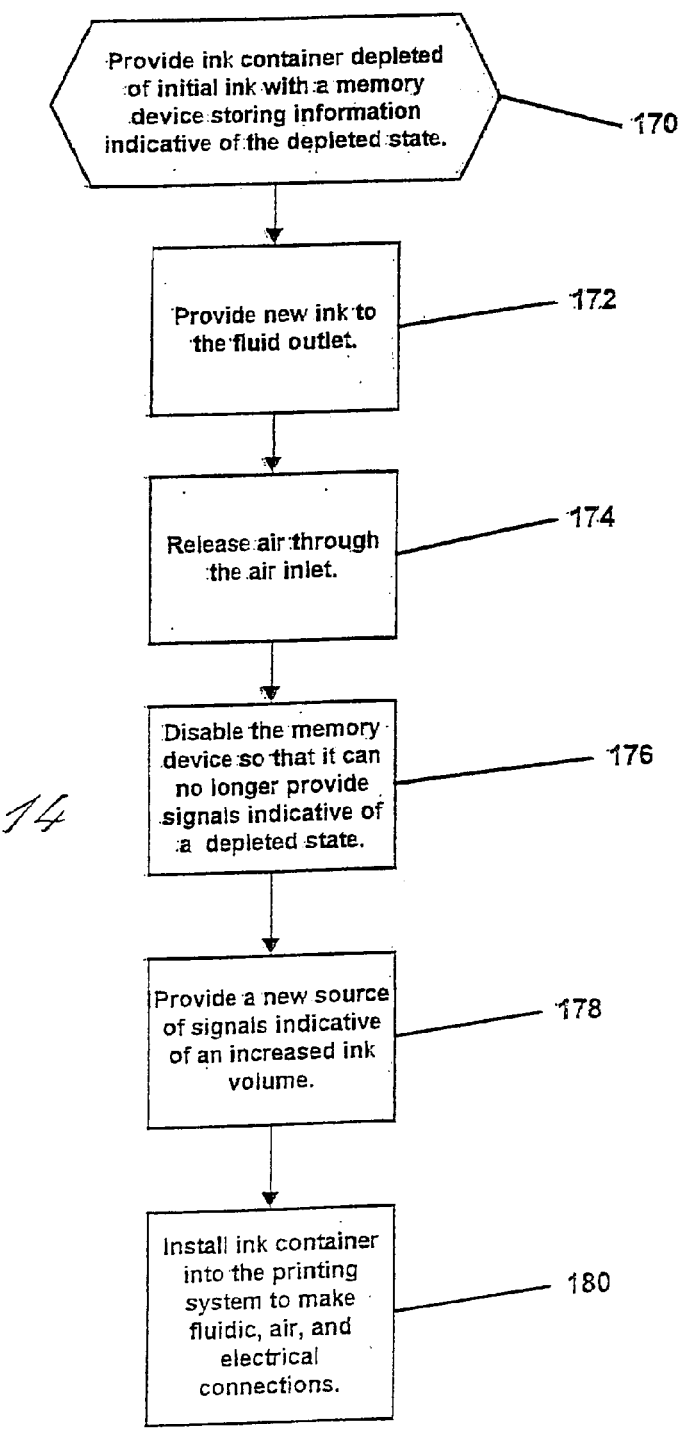
FIG. 14 is a flow chart depicting the process for refurbishing ink container 12.

Referring still to FIG. 10A, ink outlet 30 is a cylindrical member having a septum 122 on its distal end. Septum 122 has a slit for receiving needle 108. In a preferred embodiment, a check valve comprising a ball 124 and spring 126 are located in ink outlet 30 to prevent outflow of ink until needle 108 is inserted. Ball 124 seats against septum 122 and is pushed away from septum 122 by needle 108. Air inlet 28 is also a cylindrical member having a septum 128 with a slit As shown in FIGS. 11A, 11B and 14, shell 24 is a generally rectangular member with a cylindrical neck 130 on its leading end. Chassis 26 is a circular disk or plug which inserts and seals in neck 130 with the leading side of chassis 26 flush with the rim of neck 130. Reservoir 22 is a collapsible reservoir such as a collapsible bag which fits within shell 24. An opening in reservoir 22 is sealingly joined to chassis 26. Chassis 26 along with shell 24 and caps 50, 52 define a housing for reservoir 22. Shell 24 is airtight, creating a pressure chamber 132 in the space surrounding reservoir 22. Air inlet 30 communicates with pressure chamber 132. Referring to FIG. 12, rigid stiffener plates 134 are attached to opposite outer sides of reservoir 22. Outer shell 24 of ink container 12 is sealed to flexible reservoir 22 and, thus, acts as a pressure vessel. During usage, the pressurization of outer shell 24 allows pressurization of collapsible reservoir 22.

The two inductive ink volume sensor coils 36 are formed on opposite legs of flexible circuit 82. Each of the coils 36 has two leads 138 (FIG. 13) connected to one of the pairs of sensor contacts 78 (FIG. 3). One of the coils 36 locates on one side of reservoir 22 while the other is on the opposite side. When connected to printing system 10, controller 32 (FIG. 1) provides a time varying electrical current signal to one of the coils 36. This time varying electrical current induces a voltage in the other coil 36 whose magnitude varies as the separation distance between coils 36 varies. As ink is used, the opposing side wall portions of reservoir 22 collapse together, changing the electromagnetic coupling or mutual inductance of the coil pair. This change in coupling is sensed by controller 32, which infers an ink level as a result. Additionally, controller 32 also makes a continuity check when ink container 12 is installed by determining if electrical continuity exists between the two contact pads 54 leading to one of the coils 36.

Each ink container 12 has unique ink container-related aspects that are represented in the form of data provided by information storage device 34. This data is provided from ink container 12 to printing system 10 via memory device 34 automatically without requiring the user to reconfigure printer 10 for the particular ink container 12 installed. Memory device 34 has a protected section, a write-once section, and a multiple write/erase section. When the cartridge 12 is first installed in printer 10, controller 32 reads ink container information such as the manufacturer identity, part identification, system coefficients, service mode and ink supply size. Printing system 10 energizes one of coils 36 and reads an initial receiving coil voltage from the other (receiving) coil 36. This initial receiving coil voltage from receiving coil 36 is indicative of the full state of ink container 12. The printing system control electronics then records a parameter onto the protected portion of memory device 34 that is indicative of the initial receiving coil voltage. The printing system control electronics then initiates a write protect feature to assure that the information in the protected portion of memory is not altered.

The write once section is a portion of memory which can be written to by controller 32 only one time. The multiple write/erase section allows data to be written to this section more than once. Writing over data in this section is used to erase previously stored data.

Upon insertion of ink container 12 into printing system 10, controller 32 reads parameter information from memory device 34 for controlling various printing functions. For example, controller 32 uses parameter information to compute an estimate of remaining ink. If the ink remaining is less than a low ink threshold volume, a message is provided to the user indicating such. Further, when within the ink container 12 is below a threshold volume, controller 32 can disable printing system 10 to prevent operation of printhead 14 without a supply of ink. Operating printhead 14 without ink can result in reduction of printhead reliability or catastrophic failure of printhead 14.

In operation, controller 32 reads initial volume information from memory device 34 associated with ink container 12. As ink is used during printing, the ink level is monitored by controller 32, and memory device 34 is updated to contain information relating to remaining ink in ink container 12. Controller 32 thereafter monitors the level of deliverable ink in ink container 12 via memory device 34. In a preferred embodiment, data is transferred between printer 10 and memory device 34 in serial fashion using a single data line relative to ground.

In a preferred embodiment, the volume information includes the following: (1) initial supply size data in a write protected portion of memory, (2) coarse ink level data stored in write once portion of memory and (3) fine ink level data stored in a write/erase portion of memory. The initial supply size data is indicative of the amount of deliverable ink initially present in ink container 12.

The coarse ink level data includes a number of write once bits that each correspond to some fraction of the deliverable ink initially present in ink container 12. In a first preferred embodiment, eight coarse ink level bits each correspond to one-eighth of the deliverable ink initially in ink container 12. In a second preferred embodiment, to be used in the discussion that follows, seven coarse ink level bits each correspond to one-eighth of the deliverable ink initially present in ink container 12 and one coarse ink level bit corresponds to an out-of-ink condition. However, more or less coarse bits can be used, depending on the accuracy desired for a coarse ink level counter.

The fine ink level data is indicative of a fine bit binary number that is proportional to a fraction of one-eighth of the volume of the deliverable ink initially present in ink container 12. Thus, the entire range of the fine bit binary number is equivalent to one coarse ink level bit. This will be further explained below.

Printing system 10 reads the initial supply size data and calculates the amount or volume of deliverable ink initially present in ink container 12. The drop volume ejected by the printhead 14 is determined by printing system 10 based on parameters. Using the initial volume of deliverable ink in ink container 12 and the estimated drop volume of printhead 14, the printing system 10 calculates the fraction of the initial deliverable ink volume that each drop represents. This enables the printing system 10 to monitor the fraction of the initial volume of deliverable ink remaining in ink container 12.

While printing, printing system 10 maintains a drop count equal to the number of ink drops that have been ejected by printhead 14. After printing system 10 has printed a small amount, typically one page, it converts the drop count to a fine bit binary number value. This conversion utilizes the fact that the entire range of the fine bit binary number corresponds to one eighth of the initial volume of deliverable ink in ink container 12. Each time the fine bit binary number value is fully decremented or incremented, the printing system 10 writes to set one of the coarse ink level bits because each of the coarse ink level bits are in the write once section of memory device 34 these bits and corresponding ink level value cannot be altered.

Printing system 10 periodically queries the coarse and fine ink level bits to determine the fraction of the initial deliverable ink that is remaining in ink container 12. Printing system 10 can then provide a "gas gauge" or other indication to a user of printing system 10 that is indicative of the ink level in ink container 12. In a preferred embodiment, the printing system provides a "low ink warning" when the sixth coarse ink level bit is set. Also in a preferred embodiment, the printing system sets the eight (last) coarse ink level bit when the ink container 12 is substantially depleted of ink.

This last coarse ink level bit is referred to as an "ink out" bit. Upon querying the coarse ink level bits, the printing system interprets the setting of the ink out bit as an "ink out" condition for ink container 12.

The volume is sensed by the inductive sensor coils 36 (FIG. 12) only during a second phase of ink usage. During the first phase, both fine and coarse counters are used. Ink drops are counted and recorded in the fine counter portion of memory device 34. Each time the fine counter fully increments or decrements, another coarse counter bit will be set. During the second phase, only the ink level sensor coils 36 are used. The voltage output from the receiving coil 36 is compared with the voltage level indicated by the parameter recorded on memory device 34. A parameter indicative voltage output is recorded on the write/erase portion of memory. Each successive reading is compared with the previous reading as an error checking technique to allow detection of coil malfunction.

In printing system 10, the transfer of data between printer 10 and memory device 34 is in serial fashion on the single data line relative to ground. As explained above, while the ink in ink container 12 is being depleted, memory device 34 stores data which is indicative of its initial and current states. Printer 10 updates memory device 34 to indicate the volume of ink remaining. When most or substantially all of the deliverable ink has been depleted, printer 10 alters memory device 34 to allow ink container 12 to provide an "ink out" signal. Printer 10 may respond by stopping printing with ink container 12. At that point, the user will insert a new ink container 12 or an ink container which has been refurbished in accordance with this invention.

After being depleted of ink, the container 12 is potentially capable of further use if replenished with a fresh supply of ink. However, these ink containers 12 are designed for single use because of the information stored in the memory device which indicated the amount of ink that was in the reservoir prior to being refilled. If refilled and installed again on a printer, the data in the memory device 34 would still indicate the volume of ink which it contained prior to refilling. The low ink warning which the memory device 34 would signal would not be meaningful to the user because it would be inaccurate. The user would be deprived of various advantages and safeguards of the memory device. As a result, the reservoir is not designed for refilling. The present invention as will be described with respect to FIGS. 14-16 is a method and apparatus for reusing these ink containers 12.

Referring to FIG. 14, a method of the present invention is illustrated for refurbishing ink container 12. The method begins by providing an ink container 12 that is at least partially depleted of an initial ink as indicated by step 170. The ink container 12 is depleted by supplying ink to one or more inkjet printhead 14. As ink is provided to the printhead 14 the memory device 34 associated with the ink container 12 is updated with information for determining remaining ink in the ink container 12.

A source of new ink, different from the initial ink, is provided to fluid outlet 30 to refill fluid reservoir 22 as represented by step 172. Fluid reservoir 22 expands as ink is provided, displacing air in pressure chamber 132. To relieve pressure in pressure chamber 132, air is released through air inlet 28 as represented by step 174. The memory device 34 is disabled so that the memory device 34 does not provide signals to printing system 10 indicative of the depleted state as represented in step 176. A new source of signals is provided that is indicative of an increased ink volume in fluid reservoir 22 as represented in step 178. In a preferred embodiment, the new source of signals is indicative of the increased volume of ink available for printing after refill step 172. Finally, in step 180, the ink container 12 is reinstalled, establishing fluidic, air, and electrical connections between ink container 12 and printing system 10. The new ink in refilled reservoir 22 is then made available to printhead 14 via conduit 20. In addition, the new source of signals is made available to the printing system control electronics 32, and can provide information to printing system control electronics 32 that enables printing with the new ink provided by step 172.

Figure 15:
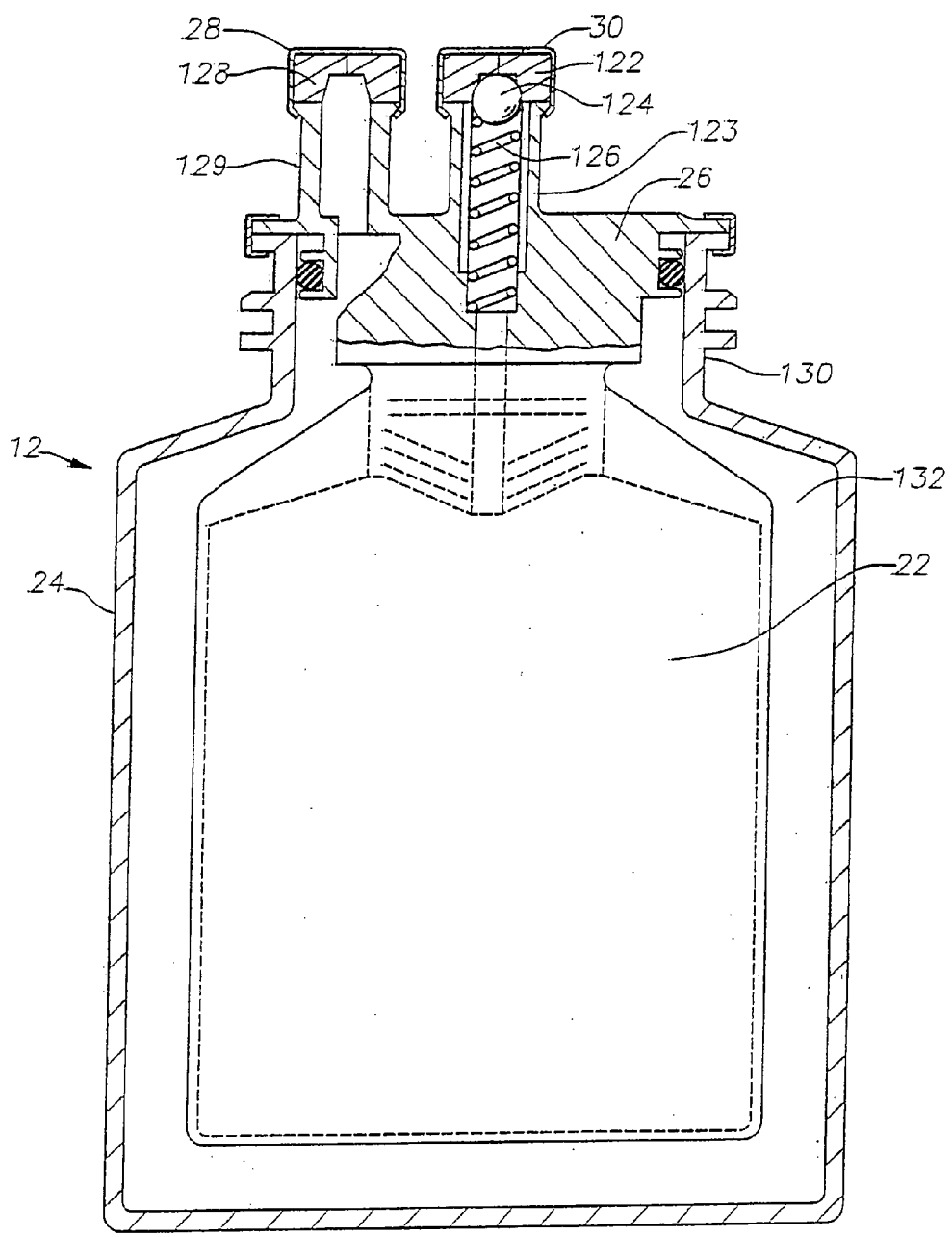
FIG. 15 is a sectional view of the ink container of FIGS. 10A and 10B, with the leading cap removed.
Figure 16:
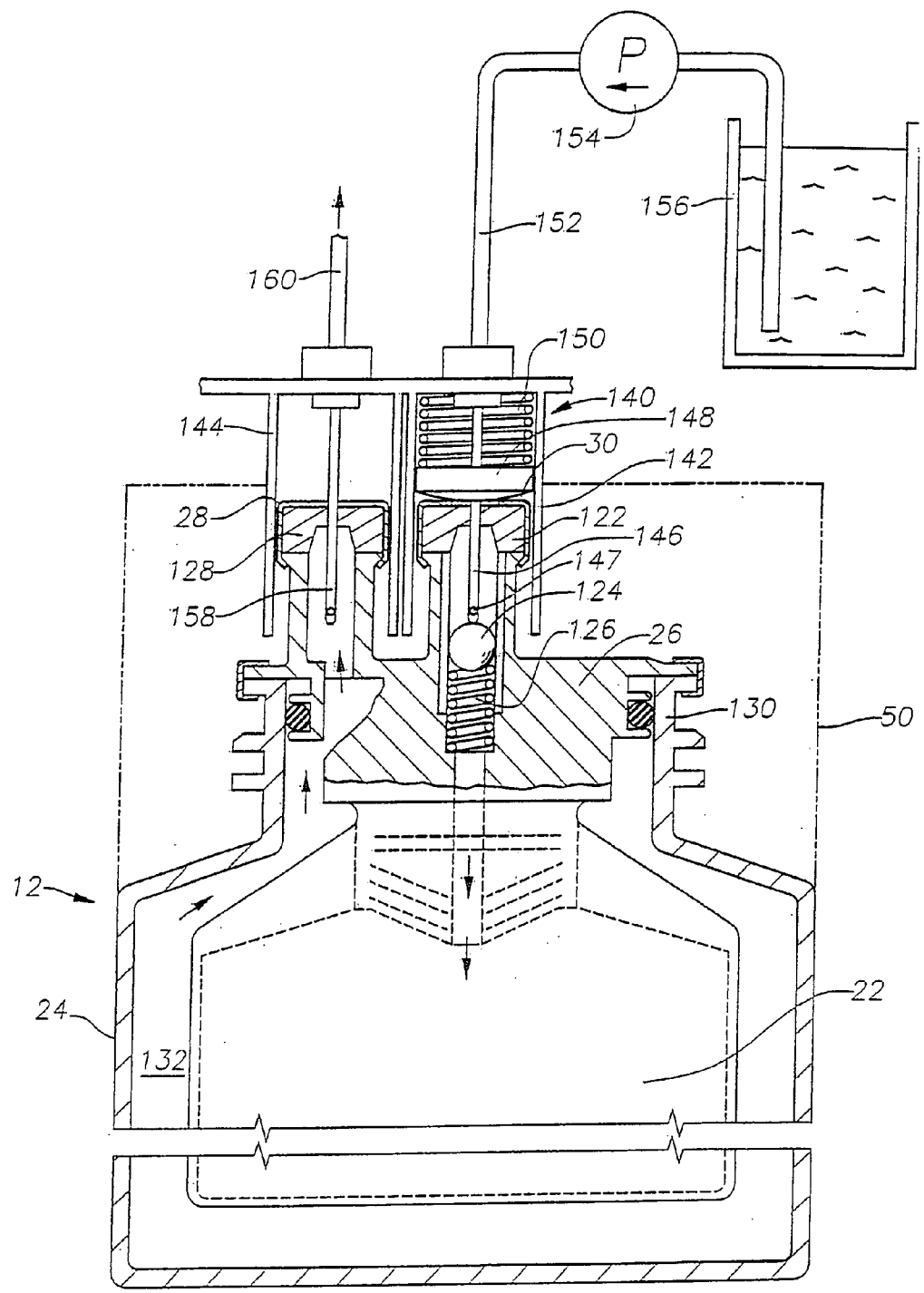
FIG. 16 is a sectional view of the ink container of FIGS. 10A, 10B, with the leading cap removed and showing the ink container being refilled with ink.

Referring now to FIGS. 15 and 16, a method and apparatus for filling ink container 12 is depicted (steps 172 and 174 of FIG. 14). To refurbish ink container 12, replacement ink is provided to collapsed reservoir 22. As replacement ink is provided, reservoir 22 expands, displacing air in pressure chamber 132 between pressure vessel 24 and reservoir 22. To avoid pressurizing pressure chamber 132 and to maximize the rate of ink flow, an air flow path is established through air inlet 28 from chamber 132 to a location outside of pressure vessel 24.

When ink is introduced into ink container 12, sealing member 124 is moved from a sealing position wherein it is in contact with septum 122 to an unsealed position wherein it is displaced linearly into hollow boss 123 in a direction away from a distal end of fluid outlet 30. At the same time, an opening or pathway is established in septum 122 by radially displacing septum 122. One way to do this is to insert a hollow conduit such as a hollow needle through septum 122 such that the hollow conduit displaces sealing member 124 linearly and displaces septum 122 radially. Next, a flow of ink is established between a source of ink and reservoir 22. Ink then flows from the source of ink, through the pathway in septum 122, past sealing member 124, through boss 123, and to reservoir 22. To enhance the flow of ink the source of ink can be pressurized.

To allow rapid air removal from pressure chamber 132 during a refill operation, an opening or pathway can be established in septum 128 by radially displacing septum 128. One way to do this is to insert a hollow conduit such as a hollow needle through septum 128. Next, a flow of air is established, such that air flows from pressure chamber 132, through hollow boss 129, through the opening in septum 128 and to an air collection region. Among various alternatives, the air collection region can be outside atmosphere or a source of vacuum. A source of vacuum applied to pressure chamber 132 will further enhance a flow of ink when refilling reservoir 22.

Referring now to FIG. 16, an exemplary embodiment of a refill apparatus for ink container 12 is depicted. A refill adapter 140 is employed which preferably has an ink sleeve 142 and a vent sleeve 144. Ink sleeve 142 and vent sleeve 144 are tubular members with open lower ends for sliding over the ink outlet 30 and air inlet 28. Ink sleeve 142 has a hollow needle 146 located therein which has a port 147 near its distal end. A seal collar 148 sealingly engages needle 146 and moves slidingly between a closed position, blocking port 147 and an open position which is shown in FIG. 16. In the open position, ink is allowed to flow through needle 146 and out port 147. A coil spring 150 urges seal collar 148 to the closed position. A conduit 152 connects needle 146 to an ink reservoir or tank 156. A pump 154 is preferably connected into conduit 152 to pump ink from tank 156 under pressure. A hollow needle 158 or tubular member is mounted in vent sleeve 144.

To refill, adapter 140 is placed on ink outlet 30 and air inlet 28. Needle 147 pierces the slit in septum 122 and pushes ball 124 downward to open the check valve. Needle 158 pierces the slit in septum 128 and vents pressure chamber 132 to atmosphere. Pump 154 is turned on to pump ink from tank 156 into reservoir 22 as indicated by the arrows. Air in pressure chamber 132 being displaced by the expansion in volume of reservoir 22 vents to atmosphere through needle 158. Once reservoir 22 is refilled, adapter 140 is removed.

In addition to refilling with ink, refurbishment (steps 176 and 178 of FIG. 14) also should be performed in regard to memory device 34 (FIG. 5) so that the benefits previously provided by memory device 34 still exist. Refurbishment of memory device 34 is discussed in more detail in U.S. patent application Ser. No. 09/034,875 incorporated herein by reference. The original memory device 34, which is located on chassis 26, provides a first source of data signals indicative of an at least partially depleted ink level state of ink container 12. More specifically and as explained above, the memory device 34 includes coarse ink level data stored in a write once portion of memory that has been altered by the printing system to reflect a reduced ink level or out of ink condition. Consequently, refilling the ink container 12 results in alteration of the amount of ink remaining but does not change the indicated coarse ink level. Therefore, the memory device 34 does not provide accurate ink remaining information resulting in improper low ink condition signals. In addition, because the refilled ink does not necessarily have the same ink parameters (i.e., composition factors such as density, colorants, solvents, additives, etc.) as those indicated by the memory device 34, then the printing system 10 may not properly compensate for this refilled ink to ensure high print quality.

To refurbish memory device 34, the pre-existing data in memory device 34 is prevented from further communication with printer 10 when cartridge 12 is installed again (step 176 of FIG. 14). In one technique, all of the data in memory device 34 is erased. This can be accomplished by exposing the memory device 34 to an energy source such as an x-ray or electric field. The energy source, if sufficient, resets the data in memory device 34. The reservoir of ink container 12 is then refilled. Then memory device 34 can be reprogrammed to reflect parameters of the refilled ink container 12. When installed in the printing system 10 the printing system operates with the ink container 12 in a manner similar to the original ink container.

In another refurbishment method, memory device 34 is disabled and replaced with a nearly identical one or with an emulator. The new memory device 34 may be an emulator or a substantial replica of the original memory device 34. An emulator is an electronic circuit that is functionally equivalent to memory device 34 for exchanging information with the printer 10. Although the emulator is functionally equivalent, structurally this device may be very different. An emulator would likely have a portion that functions as a memory and would likely provide information indicative of the volume of the reservoir 22, the type of ink, color, etc. Optionally, unlike original memory device 34, the emulator may be reset in a different manner such as whenever a new ink supply is provided. Further, the emulator may be configured to provide information to printer 10 that allows it to operate regardless of the actual condition of ink in the in reservoir 22.

The new source of signals, such as an emulator or new memory device, should be provided with the data required for proper operation of printer 10. The new source of signals should be able to communicate with printer 10 over a single wire input/output in serial fashion. This data provided by the new source of signals will be used by printer 10 to provide an indication of the volume of ink available.

In one technique for refurbishing ink container 12, the first memory device 34 will be removed from chassis 26 (FIG. 5). The substrate 86, along with memory device 34 and contact pads 80, may be pried off or otherwise removed as a unit from chassis 26. A new substrate 86, having a new memory device 34 or emulator and contact pads 80, may be secured to chassis 26 in the same place that held the original substrate 86, memory device 34 and contact pads 80. The new substrate 86 could be secured by fasteners or by adhesive. There is no need to remove volume sensing contact pads 78, which are located on flexible circuit 82 and connected to inductor coils 36.

Alternately, a substrate 86 containing only a new set of contact pads 80 may be mounted on chassis 26. The new memory device 34 or emulator may be mounted at another place on ink container 12 or remotely and connected to the new set of contact pads 80 by leads.

Another refurbishment method allows the original substrate 86, memory device 34 and contact pads 80 to remain in place. A new substrate 86, along with a new memory device 34 and contact pads 80, will be bonded on top of the original memory device 34 and contact pads 80. The material of substrate 86 is an electrical insulator. Consequently, it will insulate the new contact pads 80 from the original contact pads 80 and the electrical traces in original substrate 86 which connected the original contact pads 80 to original memory device 34. The original contact pads 80 will not be able to electrically engage printer contacts 104 (FIG. 9) because they will be covered and insulated from engagement by the new substrate 86.

In another refurbishment process, a usable portion of the original contact pads 80 remains in place and is electrically separated from the original memory device 34. In this method, preferably a cut is made through the substrate 86 transversely across contact pads 80 with a sharp object such as knife. The cut divides the substrate 86 into retained and disposable portions, the retained portion of which contains a significant portion of contact pads 80. The substrate 86 disposable portion contains memory device 34, and a small adjacent part of contact pads 80. This cut severs electrical continuity between the four terminals of memory device 34 with the part of contact pads 80 contained on the substrate 86 retained portion. Although, the size of contact pads 80 on the retained portion of substrate 86 would be smaller than the original contact pads 80, they are of adequate size to mate with printer contacts 104 (FIG. 9).

Normally, one would then remove from chassis 26 the disposable portion of substrate 86, along with the first memory device 34, and the part of contact pads 80 contained thereon. A new memory device 34 may then be mounted adjacent to or on the original contact pads 80 contained on the retained substrate portion, with its terminals connected to them. Optionally, the new memory device 34 could be mounted elsewhere on housing 72 other than cavity 80 (FIG. 7) or even remotely from printer 10 and connected to original contact pads 80 by leads. Alternately, the contact pads 80 on the retained portion of substrate 86 may be connected to leads that are attached to a remotely located emulator or memory 34.

The invention has several advantages. These alternate methods of fluidically refurbishing single-use ink containers allow them to be refilled so that it may be used several times before being discarded. By electrically refurbishing ink container 12, the volume of ink contained in reservoir 22 after refilling can be provided to printing system 10 to allow printing system 10 to monitor usage of the refill ink. In the likely event that the replacement ink used for refilling is different that the original ink (such as different colorant, solvent, additive, etc., or different concentrations of constituents) this change can be reflected by the new source of signals 34. When the ink container with the new source of signals 34 is installed in printing system 10, the printing system 10 can also alert the user regarding the change in ink. This can be in the form of a message displayed by the printing system 10 or a computer screen that is indicative of the type or origin of ink installed. Such a message may indicate whether or not the ink contained in reservoir 22 is of known origin or composition.

While the invention has been shown or described in only some of its forms, it should be apparent to those skilled in the art that it is not so limited, but is susceptible to various changes without departing from the scope of the invention.

What is claimed is:

1. A refurbished ink container adapted for installation into an inkjet printing system, the printing system configured to receive signals conveying information about the refurbished ink container, the ink container comprising:
 a pressure vessel surrounding a supply of ink, the supply of ink including a volume of a refill ink added to an at least partially depleted volume of an initial ink; and
 a refurbished source of signals configured to send signals conveying information about the refurbished ink container to the printing system, wherein the information enables printing when the refurbished ink container is releasably installed into the printing system, and wherein the information conveyed by the refurbished source of signals is indicative of an increase in a volume of the supply of ink caused by addition of the volume of the refill ink to the at least partially depleted volume of the initial ink.

2. The refurbished ink container of claim 1, wherein the refurbished source of signals is indicative of the refill ink in the supply of ink.

3. The refurbished ink container of claim 1, wherein the refurbished source of signals is a replacement for an initial source of signals.

4. The refurbished ink container of claim 1, wherein the supply of ink comprises a collapsible reservoir, the pressure vessel surrounding at least a portion of the collapsible reservoir.

5. A refurbished ink container adapted for installation into an inkjet printing system, the inkjet printing system configured to receive signals conveying information about the refurbished ink container, the ink container comprising:
 a pressure chamber surrounding a collapsible ink reservoir, the ink reservoir including a refill ink added to an at least partially depleted initial ink;
 means for adding the refill ink into the collapsible ink reservoir;
 an air fitting in fluid communication with an interior of the pressure chamber for releasing air within the pressure chamber to atmosphere as the refill ink is added into the collapsible ink reservoir; and
 a refurbished source of signals configured to send signals conveying information about the refurbished ink container to the printing system, wherein the information enables printing when the refurbished ink container is installed into the printing systems, wherein the refurbished source of signals is indicative of an increase in a volume of the supply of ink caused by adding the refill ink into the collapsible ink reservoir.

6. The refurbished ink container of claim 5, wherein the air fitting admits air into the pressure chamber to expel ink from the collapsible ink reservoir.

7. The refurbished ink container of claim 5, wherein the source of signals is indicative of the refill ink in the collapsible ink reservoir.

8. The refurbished ink container of claim 5, wherein the refurbished source of signals is a replacement for an initial source of signals.

9. The refurbished ink container of claim 5, wherein the collapsible ink reservoir contains a portion of the initial ink and the refill ink.

10. The refurbished ink container of claim 9, wherein the refill ink is added to the collapsible ink reservoir prior to the collapsible ink reservoir being fully depleted of the initial ink.

11. A method for refilling a printer ink container for providing ink, to an ink jet printhead of an ink jet printing system, the ink container in an at least partially depleted of initial ink condition, the ink container having a sealed housing, a flexible ink reservoir located within the housing, an ink outlet on the housing and in fluid communication with the ink reservoir, with the ink outlet being removably connectable to a fluid inlet in fluid communication with the ink jet printhead of the ink jet printing system upon insertion of the housing into the ink jet printing system, an air inlet on the housing and in fluid communication with a space between the housing and the ink reservoir, with the air inlet being removably connectable to an air outlet of the ink jet printing system upon insertion of the housing into the ink jet printing system, and a source of signals conveying information to the inkjet printing system, the information indicative of the at least partially depleted of initial ink condition of the ink container, the method comprising:
 (a) refilling the ink reservoir with a refill ink from a source of refill ink through the ink outlet; and
 (b) releasing air from the space between the housing and the ink reservoir and through the air inlet; and
 (c) refurbishing the source of signals to convey information indicative of a refilled condition of the ink container and thereby enable printing when the refilled ink container is installed into the ink jet printing system.

12. The method of claim 11, wherein step (a) comprises refilling the ink reservoir with a pressurized source of the refill ink.

13. The method of claim 11 wherein step (b) comprises releasing the air to atmosphere as the ink reservoir is refilled with the refill ink.

14. The method of claim 11, wherein the step (b) comprises applying a vacuum to the space between the housing and the ink reservoir to establish a flow of ink from the source of refill ink to the ink reservoir.

15. The method of claim 11, wherein refurbishing the source of signals comprises altering the source of signals to indicate an increased volume of ink in the ink container.

16. The method of claim 15, wherein altering the source of signals comprises replacing an initial source of signals indicative of the at least partially depleted of initial ink condition with a different source of signals indicative of an increased volume of ink in the ink container.

17. The method of claim 11, wherein refurbishing the source of signals comprises altering the source of signals to indicate the refill ink in the ink container.

* * * * *

UNITED STATES PATENT AND TRADEMARK OFFICE
CERTIFICATE OF CORRECTION

| | | |
|---|---|---|
| PATENT NO. | : 7,249,831 B2 | Page 1 of 1 |
| APPLICATION NO. | : 10/426332 | |
| DATED | : July 31, 2007 | |
| INVENTOR(S) | : Winthrop D. Childers et al. | |

It is certified that error appears in the above-identified patent and that said Letters Patent is hereby corrected as shown below:

On the title page, item (63), under "Related U.S. Application Data", lines 1-2, delete "Continuation of application No. 09/951,114, filed on Sep. 13, 2001, now Pat. No. 7,008,050, and a"

On the title page, item (63), under "Related U.S. Application Data", lines 8-9, after "5,825,387," delete "application No. 10/426,332,"

On the title page, item (63), under "Related U.S. Application Data", line 11, after "6,074,050," delete "application No. 10/426,332,"

On the title page, item (63), under "Related U.S. Application Data", line 16, after "5,812,156," delete "application No. 10/426,332,"

In column 13, line 64, in Claim 5, delete "systems" and insert -- system --, therefor.

In column 14, line 32, in Claim 11, delete "conveving" and insert -- conveying --, therefor.

Signed and Sealed this

Second Day of September, 2008

JON W. DUDAS
*Director of the United States Patent and Trademark Office*